US012582384B2

(12) United States Patent
Okamoto et al.

(10) Patent No.: US 12,582,384 B2
(45) Date of Patent: Mar. 24, 2026

(54) ULTRASOUND IMAGING PROBE FOR HIFU RADIATION DEVICE, AND ULTRASOUND IMAGE DISPLAY DEVICE

(71) Applicant: SONIRE THERAPEUTICS INC., Tokyo (JP)

(72) Inventors: Jun Okamoto, Tokyo (JP); Tohru Satoh, Tokyo (JP); Tsuyoshi Ueyama, Tokyo (JP)

(73) Assignee: Sonire Therapeutics Inc., Tokyo (JP)

( * ) Notice: Subject to any disclaimer, the term of this patent is extended or adjusted under 35 U.S.C. 154(b) by 9 days.

(21) Appl. No.: 18/289,522

(22) PCT Filed: Mar. 22, 2022

(86) PCT No.: PCT/JP2022/013243
§ 371 (c)(1),
(2) Date: Nov. 3, 2023

(87) PCT Pub. No.: WO2023/139805
PCT Pub. Date: Jul. 27, 2023

(65) Prior Publication Data
US 2024/0225604 A1      Jul. 11, 2024

(30) Foreign Application Priority Data
Jan. 18, 2022      (JP) ................................. 2022-005979

(51) Int. Cl.
*A61B 8/00*      (2006.01)
*A61N 7/02*      (2006.01)

(52) U.S. Cl.
CPC ............ *A61B 8/463* (2013.01); *A61B 8/4218* (2013.01); *A61B 8/4281* (2013.01); *A61N 7/02* (2013.01)

(58) Field of Classification Search
CPC ..... A61B 8/463; A61B 8/4218; A61B 8/4281; A61B 8/00; A61B 8/14; A61B 17/00; A61B 8/4444; A61N 7/02; A61N 7/00
See application file for complete search history.

(56) References Cited

U.S. PATENT DOCUMENTS

2013/0296707 A1* 11/2013 Anthony .............. A61B 8/4254
600/459
2015/0148664 A1    5/2015 Stolka et al.
(Continued)

FOREIGN PATENT DOCUMENTS

JP        H0871069 A        3/1996
JP        H09182196 A       7/1997
(Continued)

OTHER PUBLICATIONS

JP-2002238898 machine translation (Year: 2002).*
(Continued)

*Primary Examiner* — Alexei Bykhovski
(74) *Attorney, Agent, or Firm* — ICE MILLER LLP; Justin D. Swindells

(57)        ABSTRACT

Apparatus and method to clearly indicate the direction of an observation plane of an ultrasound imaging probe to a practitioner. This ultrasound imaging probe includes a probe tip at which ultrasound waves are transmitted and received. An indicator of the direction of the observation plane in which an ultrasound image is acquired is applied to the probe tip. The indicator may be a color applied to the surface of a housing. The ultrasound imaging probe is carried by a carrying mechanism.

9 Claims, 4 Drawing Sheets

(56)               References Cited

U.S. PATENT DOCUMENTS

| | | |
|---|---|---|
| 2017/0303892 A1 | 10/2017 | Antol et al. |
| 2019/0216429 A1* | 7/2019 | Sakai ................... A61B 8/4461 |
| 2021/0212709 A1 | 7/2021 | Pernot et al. |
| 2021/0298719 A1 | 9/2021 | Elevelt et al. |

FOREIGN PATENT DOCUMENTS

| | | | |
|---|---|---|---|
| JP | 2002238898 A | * | 8/2002 |
| JP | 2006087599 A | | 4/2006 |
| JP | 2009050511 A | | 3/2009 |
| JP | 2018015144 A | | 2/2018 |
| JP | 2020022680 A | | 2/2020 |
| JP | 2020062205 A | * | 4/2020 |

OTHER PUBLICATIONS

JP-2020062205 machine translation (Year: 2020).*
Complementary Colors; Interaction Design Foundation; https://www.interaction-design.org/literature/topics/complementary-colors?srsltid=AfmBOorS3hdSy3FNPihiraRxF-W5AI0H_OAC4xM8U3M6nZj0hVoe7wx0; 2025 (Year: 2025).*
Lifehacker, "Learning about combinations that go well together based on the basics of color theory," Aug. 17, 2014, https://www.lifehacker.jp/article/140817color/ (8 pages).
"Complimentary Colors," Japanese Wikipedia, https://ja.wikipedia.org/wiki/%E8%A3%90%E8%89%B2 (2 pages).
Notice of Grounds for Rejection issued in JP Application No. 2022-005979 on May 24, 2022 and English translation (7 pages).
International Search Report (w/translation) and Written Opinion issued in PCT/JP2022/013243, mailed May 31, 2022 (9 pages).
Extended European Search Report issued in corresponding Europe Application No. 22921001.8 mailed Dec. 1, 2025.

* cited by examiner

ULTRASOUND IMAGING PROBE FOR HIFU RADIATION DEVICE, AND ULTRASOUND IMAGE DISPLAY DEVICE

CROSS REFERENCE TO RELATED APPLICATIONS

This application is a National Stage of International Patent Application No. PCT/JP2022/013243, filed on Mar. 22, 2022, which claims priority to Japanese Patent Application No. JP 2022-005979, filed on Jan. 18, 2022, the disclosures of which are incorporated by reference in their entireties.

TECHNICAL FIELD

The present invention relates to an ultrasound imaging probe and an ultrasound image display device, and more particularly to an improvement in an ultrasound imaging probe.

BACKGROUND

A treatment device which uses high-intensity focused ultrasound has been widely used. The treatment device is referred to as a HIFU radiation device or a HIFU radiation system (high intensity focused ultrasound) and necrotizes a tissue by irradiating a treatment site with an ultrasound wave.

In general, a HIFU radiation device includes plural ultrasonic transducers disposed on a bowl-shaped surface. The plural ultrasonic transducers are disposed such that one point is irradiated with an ultrasound wave emitted from each of those and a focal point is formed. In a treatment, a position of the focal point is set to the treatment site, and irradiation with an ultrasound wave is performed. For a check of an irradiation position, an ultrasound diagnostic device is used which indicates the focal point in an ultrasound image.

The following Patent Document 1 discloses an ultrasound treatment device that observes a position of a focal point by using an ultrasound diagnostic device which displays a B-mode image (tomographic image). In this device, an ultrasound wave at a low level at which tissues are not influenced is emitted from ultrasonic transducers for treatment, and a tomographic image is displayed by transmission and reception of an ultrasound wave by an ultrasound imaging probe. Because acoustic characteristics of the tissues of a test subject change in accordance with a change in a temperature of the tissues, the position of the focal point is indicated in the tomographic image by a magnitude of luminance.

As an ultrasound probe related to the invention of the present application, the following Patent Document 2 discloses an ultrasound probe which is provided with an illumination function of making bright a wave sending direction side of an ultrasound wave by illumination of light. Patent Document 3 discloses an ultrasound probe which is provided with a thermolabel whose color changes when a predetermined temperature is reached.

CITATION LIST

Patent Literature

Patent Document 1: JP Hei 8-71069 A
Patent Document 2: JP 2009-50511 A

Patent Document 3: JP Hei 9-182196 A

Non Patent Literature

Non Patent Document 1: Lifehacker [Japanese Edition], "Learning about combinations that go well together based on the basics of color theory", Aug. 17, 2014, Internet, <https://www.lifehacker.jp/article/140817color/>.
Non Patent Document 2: Article on "Complementary Colors" in the Japanese Wikipedia, Internet, <https://ja.wikipedia.org/wiki/% E8% A3%9C % E8%89% B2>.

SUMMARY

Technical Problem

In general, in high-intensity focused ultrasound, a B-mode image is acquired by transmission and reception of an ultrasound wave by an ultrasound imaging probe, and a body tissue of a patient is thereby observed. As for the ultrasound imaging probe, a relationship is structurally defined between an orientation of an observation surface (a direction which the observation surface faces) through which an ultrasound image such as the B-mode image is acquired and a posture of the ultrasound imaging probe. However, there may be a case where only by a visual check of the ultrasound probe, it is difficult for a practitioner to recognize the orientation of the observation surface.

It is an advantage of the present invention to clearly indicate an orientation of an observation surface of an ultrasound imaging probe for a practitioner.

Solution to Problem

The present invention provides an ultrasound imaging probe for a HIFU radiation device, the ultrasound imaging probe including a probe distal end to and from which an ultrasound wave is transmitted and received, and a coupling bag formed of a light transmitting material and configured to retain a liquid between the probe distal end and a patient, the probe distal end being located inside the coupling bag, in which when a surface where the ultrasound wave is transmitted and received in the probe distal end is defined as a lower surface, a front surface and a rear surface of the probe distal end are colored with different colors from each other, or a left side surface and a right side surface are colored with different colors from each other, and the ultrasound imaging probe is transported by a transport mechanism.

The present invention provides, in an aspect, an ultrasound imaging probe for a HIFU radiation device, the ultrasound imaging device including a probe distal end to and from which an ultrasound wave is transmitted and received, and a coupling bag formed of a light transmitting material and configured to retain a liquid between the probe distal end and a patient, the probe distal end being located inside the coupling bag, in which when a surface where the ultrasound wave is transmitted and received in the probe distal end is defined as a lower surface, a front surface, a rear surface, a left side surface, and a right side surface of the probe distal end are colored with different colors from each other, and the ultrasound imaging probe is transported by a transport mechanism.

The probe distal end desirably has a front surface and a rear surface which are colored with complementary colors to each other, or has a left side surface and a right side surface which are colored with complementary colors to each other.

The present invention provides, in another aspect, an ultrasound imaging probe for a HIFU radiation device, the ultrasound imaging probe including a probe distal end to and from which an ultrasound wave is transmitted and received, in which in the probe distal end, one of housing surfaces is provided with a color serving as an indicator that indicates an orientation of an observation surface through which an ultrasound image is acquired, the probe distal end has, in the housing surfaces, a pair of housing surfaces facing opposite directions, and one of the pair of housing surfaces and the other of the pair of housing surfaces are colored with complementary colors to each other, and the ultrasound imaging probe is transported by a transport mechanism.

The ultrasound imaging probe desirably includes a coupling bag which retains a liquid between the probe distal end and a patient, and the coupling bag is formed of a light transmitting material.

Further, the present invention provides an ultrasound image display device for a HIFU radiation device, the ultrasound image display device including: the ultrasound imaging probe; and an image display processing unit which generates image data based on the ultrasound wave received by the ultrasound imaging probe and displays the ultrasound image based on the image data, in which the image display processing unit causes an ultrasound image displayed on the image displaying processing unit to include figures which indicate a correspondence between a direction on an observation surface through which the ultrasound image is acquired and a direction on the probe distal end.

Advantageous Effects of Invention

In the present invention, an orientation of an observation surface of an ultrasound imaging probe may clearly be indicated for a practitioner.

DESCRIPTION OF EMBODIMENTS

Figure 1:
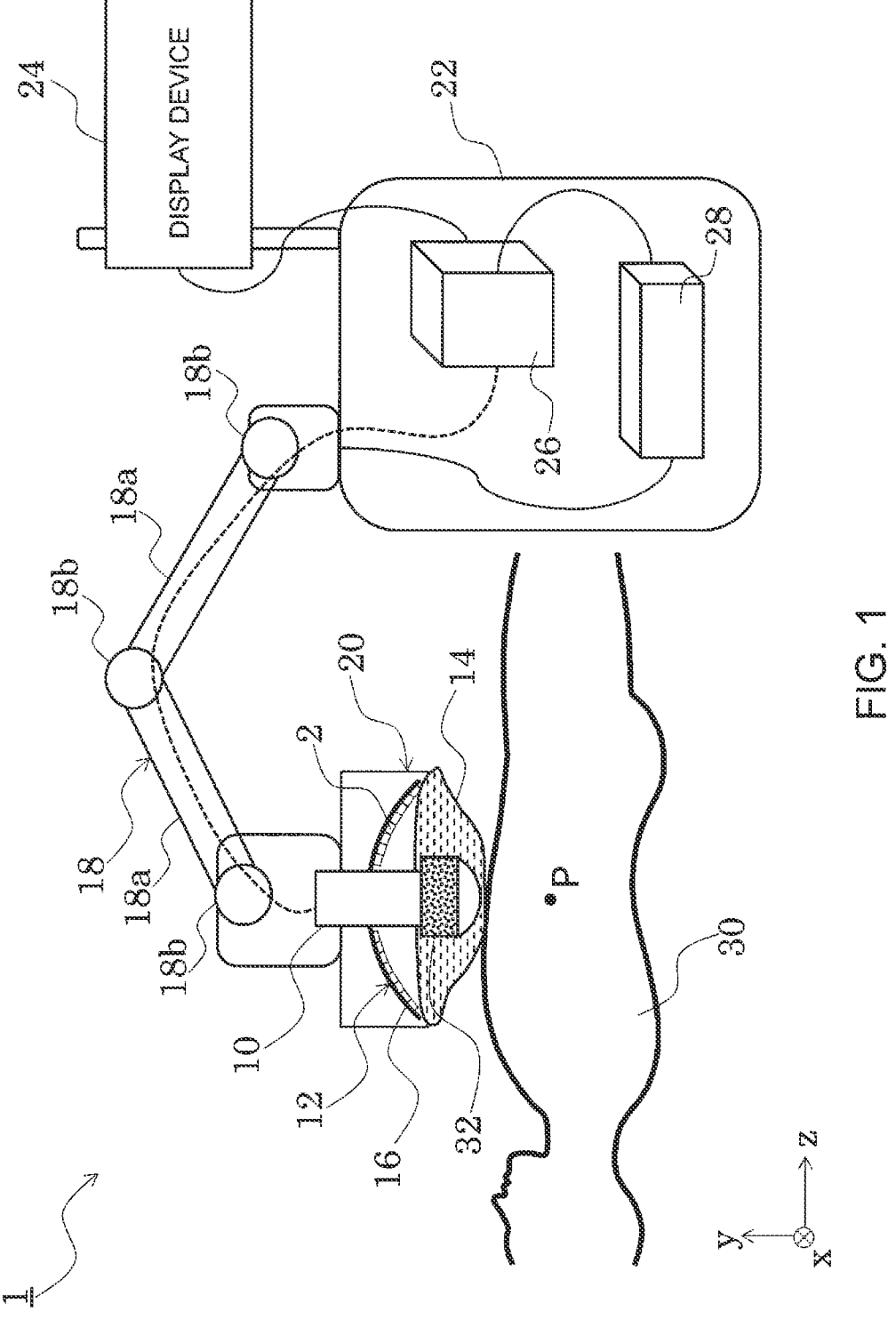
FIG. 1 is a diagram illustrating a configuration of a HIFU radiation system.

An embodiment of the present invention will be described with reference to drawings. The same configuration elements which are illustrated in plural drawings are provided with the same reference characters, and repeated descriptions thereof will be omitted. Further, terms such as up, down, left, and right in the present specification indicate directions in the drawings. The terms representing the directions are used for convenience of description and do not limit postures in arrangement of the configuration elements.

FIG. 1 illustrates a configuration of a HIFU radiation system 1 according to the embodiment of the present invention. The HIFU radiation system 1 includes an ultrasound imaging probe 10 (hereinafter referred to as ultrasound probe 10), a HIFU transducer unit 12, a coupling bag 14, a robot arm 18, a controller 22, and a display device 24. In FIG. 1, a surface through which an ultrasound image such as a B-mode image is to be observed (observation target surface) in a patient 30 is set as a surface parallel to a yz coordinate plane, and a coordinate axis perpendicular to the yz coordinate plane is set as an x axis.

The HIFU transducer unit 12 includes a bowl-shaped transducer housing 16 whose opening faces downward and plural ultrasonic transducers 2 fixed to the transducer housing 16. A shape of the transducer housing 16 may be a similar shape to a side surface of a cone. Here, a cone denotes a three-dimensional shape which is formed with a set of straight lines extending from one point in a space to a bottom surface. Each of the ultrasonic transducers 2 is fixed to the transducer housing 16 such that an intensity of an ultrasound wave is increased at a treatment reference point P below the transducer housing 16 when each of the ultrasonic transducers 2 emits an ultrasound wave. That is, each of the ultrasonic transducers 2 is fixed to the transducer housing 16 so as to form a focal point at the treatment reference point P.

The ultrasound probe 10 is mounted on the transducer housing 16 such that the ultrasound wave is transmitted and received in a position below the transducer housing 16 and above the treatment reference point P. In the present embodiment, the ultrasound probe 10 passes, in an up-down direction, through the apex of the transducer housing 16, and a probe distal end 32 for transmitting and receiving the ultrasound wave is directed downward. The ultrasound probe 10 has directivity, and the ultrasound wave is transmitted and received through an observation surface which faces a direction corresponding to a structure of the ultrasound probe 10. The ultrasound probe 10 may be movable in the up-down direction. Further, the ultrasound probe 10 may be rotatable around an axis in a longitudinal direction as a center.

Below the HIFU transducer unit 12, there is provided the coupling bag 14 which matches acoustic impedances between each of the ultrasonic transducers 2 and the patient 30 and between the ultrasound probe 10 and the patient 30. The coupling bag 14 may be a bag which is filled with a liquid such as water. The coupling bag 14 retains a liquid between the ultrasound probe 10 and the patient 30. The coupling bag 14 is formed of a light transmitting material, and is transparent or semi-transparent. The ultrasound probe 10 can be seen through from an outside of the coupling bag 14.

The ultrasound probe 10, the HIFU transducer unit 12, and the coupling bag 14 are mounted on a distal end of the robot arm 18 as a transport mechanism. The robot arm 18 is configured with plural arms 18a which are connected together by joints 18b and is mounted on a housing of the controller 22 via the joint 18b. Each of the arms 18a swings about the joint 18b as a rotation axis, and the robot arm 18 thereby transports a movable body 20, which includes the ultrasound probe 10, the HIFU transducer unit 12, and the coupling bag 14, in three directions of x axis, y axis, and z axis.

The controller 22 includes a HIFU control unit 26 and a robot control unit 28. The HIFU control unit 26 includes a computer, an electric circuit for controlling the ultrasound probe 10, and an electric circuit for controlling the HIFU transducer unit 12. The computer included in the HIFU control unit 26 may be a business computer, a personal computer, a tablet computer, or the like. The computer executes programs and thereby executes a process for generating each image and a process for displaying each image.

With the HIFU control unit 26, an operation apparatus (not illustrated) is connected by which a user operates the HIFU radiation system 1. The operation apparatus may include a mouse, a touch panel integrated with the display device 24, a switch, a keyboard, and so forth.

The HIFU control unit 26 executes a process for causing the ultrasound probe 10 and the HIFU transducer unit 12 to act. For example, the HIFU control unit 26 causes the ultrasound probe 10 to transmit and receive the ultrasound wave, generates B-mode image data based on a reception signal based on the ultrasound wave received by the ultrasound probe 10, and causes the display device 24 to display the B-mode image. Further, the HIFU control unit 26 causes each of the ultrasonic transducers 2 included in the HIFU transducer unit 12 to transmit an ultrasound wave for treatment.

The robot control unit 28 may control the robot arm in accordance with control by the HIFU control unit 26 and may cause the robot arm 18 to transport the movable body 20. Further, the robot control unit 28 may include an operation apparatus. In this case, the robot control unit 28 may control the robot arm 18 in accordance with an operation of the operation apparatus by the user.

Before the HIFU transducer unit 12 irradiates the patient 30 with the ultrasound wave for treatment, the following positioning process may be executed. The HIFU control unit 26 causes each of the ultrasonic transducers 2 to transmit an ultrasound wave at a lower intensity than that in treatment. A position and a posture of the ultrasound probe 10 are set to a position and a posture in which the observation surface of the ultrasound probe 10 matches the observation target surface of the patient 30. The HIFU control unit 26 causes the ultrasound probe 10 to scan, by an ultrasound beam, the observation target surface of the patient 30 and thereby acquires the B-mode image data. The HIFU control unit 26 causes the display device 24 to display the B-mode image. The user as a practitioner refers to the B-mode image displayed on the display device 24 and checks a different between the focal point of the ultrasound wave transmitted from the HIFU transducer unit 12 and a position of an affected part.

When the difference between a position of the focal point and the position of the affected part is not in a permissible range, the user causes the robot arm 18 to act to change positions and postures of the ultrasound probe 10 and the HIFU transducer unit 12. The user checks that the position of the focal point matches the position of the affected part and thereafter performs an operation for treatment by the HIFU control unit 26. The HIFU control unit 26 causes each of the ultrasonic transducers 2 to transmit a treatment ultrasound wave having an intensity necessary for treatment in accordance with the operation by the user. Accordingly, a body tissue is cauterized at the focal point, and the treatment is practiced.

Figures 2A, 2B:
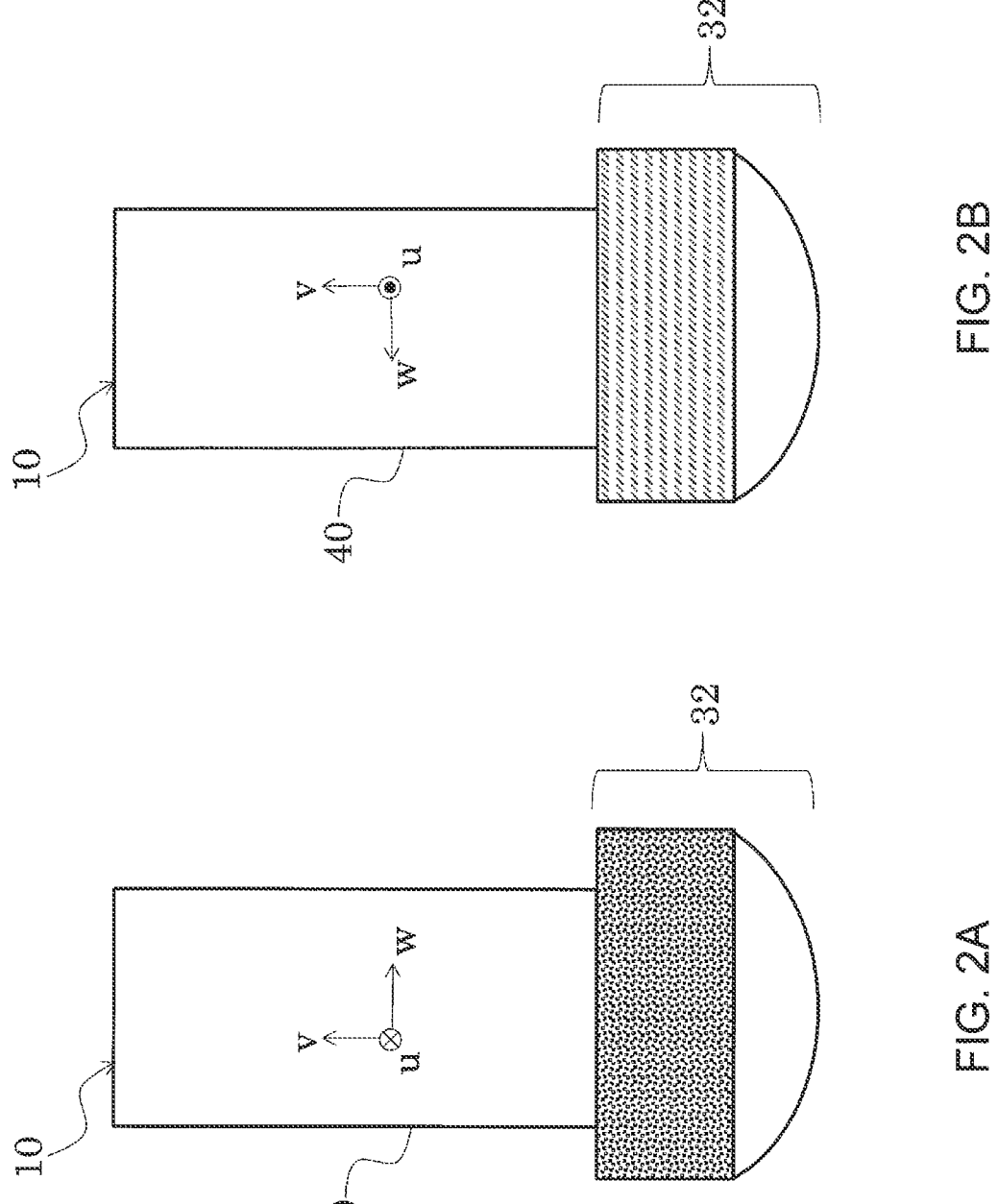
FIG. 2A is a diagram illustrating a configuration of an ultrasound probe.
FIG. 2B is a diagram illustrating the configuration of the ultrasound probe.

Colors as indicators, which indicate an orientation of the observation surface through which the ultrasound image is acquired, are provided to the probe distal end 32 of the ultrasound probe 10. FIG. 2A and FIG. 2B illustrate a configuration of the ultrasound probe 10. The ultrasound probe 10 includes the probe distal end 32 and a support portion 40 which supports the probe distal end 32. Plural ultrasonic transducers are arrayed in a housing of the probe distal end 32, an ultrasound wave is transmitted from a lower surface of the probe distal end 32, and the ultrasound wave is received by the lower surface of the probe distal end 32.

FIG. 2A and FIG. 2B illustrates a uvw coordinate system which is fixed to the ultrasound probe 10. The ultrasound probe 10 transmits and receives the ultrasound wave on a plane parallel with a vw coordinate plane. That is, the observation surface of the ultrasound probe 10 is parallel with the vw coordinate plane, and a normal direction of the observation surface is oriented in a u-axis positive direction and a u-axis negative direction.

The housing of the probe distal end 32 has a shape in which arch shapes swelling downward are joined together below a substantially rectangular cuboid shape. Here, the arch shape is a three-dimensional shape which exhibits an arc-shaped surface swelling downward in a plane parallel with the vw coordinate plane. A housing of the support portion 40 has a substantially quadrangular prism shape, and its lower end is joined to an upper surface of the probe distal end 32. The housing of the probe distal end 32 and the housing of the support portion 40 may be integrally formed.

FIG. 2A illustrates a diagram in which the ultrasound probe 10 is viewed while a line of sight is directed in the u-axis positive direction. That is, FIG. 2A illustrates a housing surface (rear surface) which is directed in the u-axis negative direction. FIG. 2B illustrates a diagram in which the ultrasound probe 10 is viewed while the line of sight is directed in the u-axis negative direction. That is, FIG. 2B illustrates the housing surface (front surface) which is directed in the u-axis positive direction. Among the housing surfaces of the probe distal end 32, the front surface and the rear surface of a substantially rectangular cuboid shaped portion are colored with different colors from each other. However, FIG. 2A and FIG. 2B express a difference between colors by a difference between monochrome fill patterns. The color provided to the front surface and the color provided to the rear surface may have a relationship of complementary colors. Here, complementary colors denote a combination of two chromatic colors which can make an achromatic color when mixed. Complementary colors have effects of emphasizing each other and of enabling each other to appear vivid. As for complementary colors, the above Non Patent Documents 1 and 2 have descriptions.

Figure 3B:
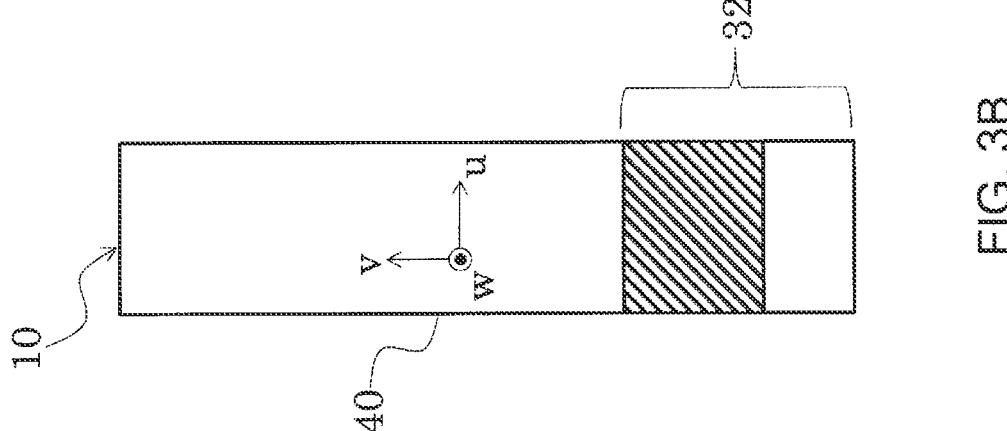
FIG. 3B is a diagram illustrating the configuration of the ultrasound probe.
Figure 3A:
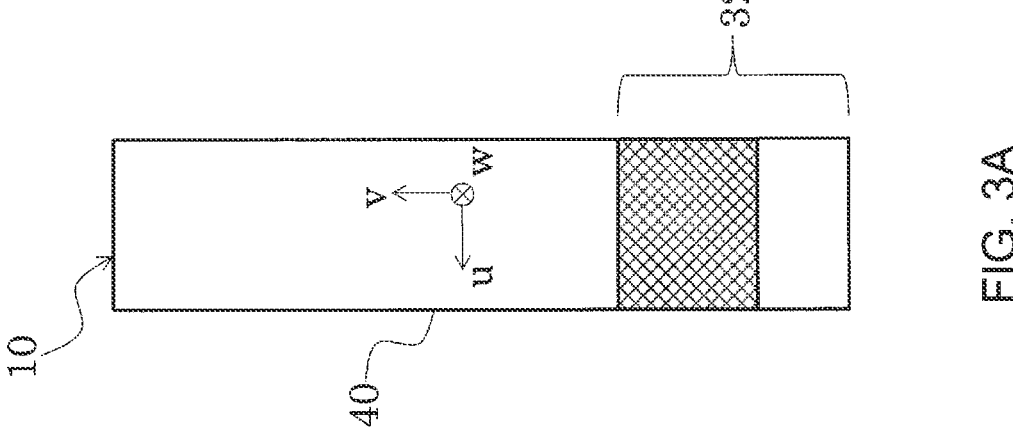
FIG. 3A is a diagram illustrating the configuration of the ultrasound probe.

FIG. 3A illustrates a diagram in which the ultrasound probe 10 is viewed while the line of sight is directed in a w-axis positive direction. That is, FIG. 3A illustrates the housing surface (left side surface) which is directed in a w-axis negative direction. FIG. 3B illustrates a diagram in which the ultrasound probe 10 is viewed while the line of sight is directed in the w-axis negative direction. That is, FIG. 3B illustrates the housing surface (right side surface) which is directed in the w-axis positive direction. Among the housing surfaces of the probe distal end 32, the right side surface and the left side surface of the substantially rectangular cuboid shaped portion are provided with different colors from each other. However, FIG. 3A and FIG. 3B express a difference between colors by a difference between monochrome fill patterns. The color provided to the right side surface and the color provided to the left side surface may be complementary colors to each other.

The pair of colors provided to the front surface and the rear surface may be different from the colors provided to the right side surface and the left side surface. For example, in a case where the pair of colors provided to the right side surface and the left side surface are set as the complementary colors to the pair of colors provided to the front surface and the rear surface, the pair of colors provided to the right side surface and the left side surface and the pair of colors provided to the front surface and the rear surface may be in relationships of an angle of 90° in a color circle (Non Patent Documents 1 and 2). Further, colors indicating directivity of the ultrasound probe 10 do not have to be provided to the right side surface and the left side surface. That is, a color of a material or a color of a substrate of the housing surface may appear on the right side surface and the left side surface.

As described above, the probe distal end 32 has a pair of housing surfaces which face opposite directions, and one of the pair of housing surfaces and the other of the pair of housing surfaces are colored with different colors from each other. A color does not have to be provided to one or the other of the pair of housing surfaces, and the color of the material or the color of the substrate of the housing surface may appear. In such a configuration of the ultrasound probe 10, the orientation of the observation surface of the ultrasound probe 10 is easily perceived by the user. Accordingly, it becomes easy to match the observation surface of the ultrasound probe 10 with the observation target surface of the patient 30.

Here, a description is made about a configuration in which as the indicators which indicate the orientation of the observation surface through which the ultrasound image is acquired, the pair of housing surfaces facing opposite directions are colored with different colors from each other. Other than such a configuration, the pair of housing surfaces which face opposite directions may be provided with different figures, different identification marks from each other, or the like.

Figure 4:
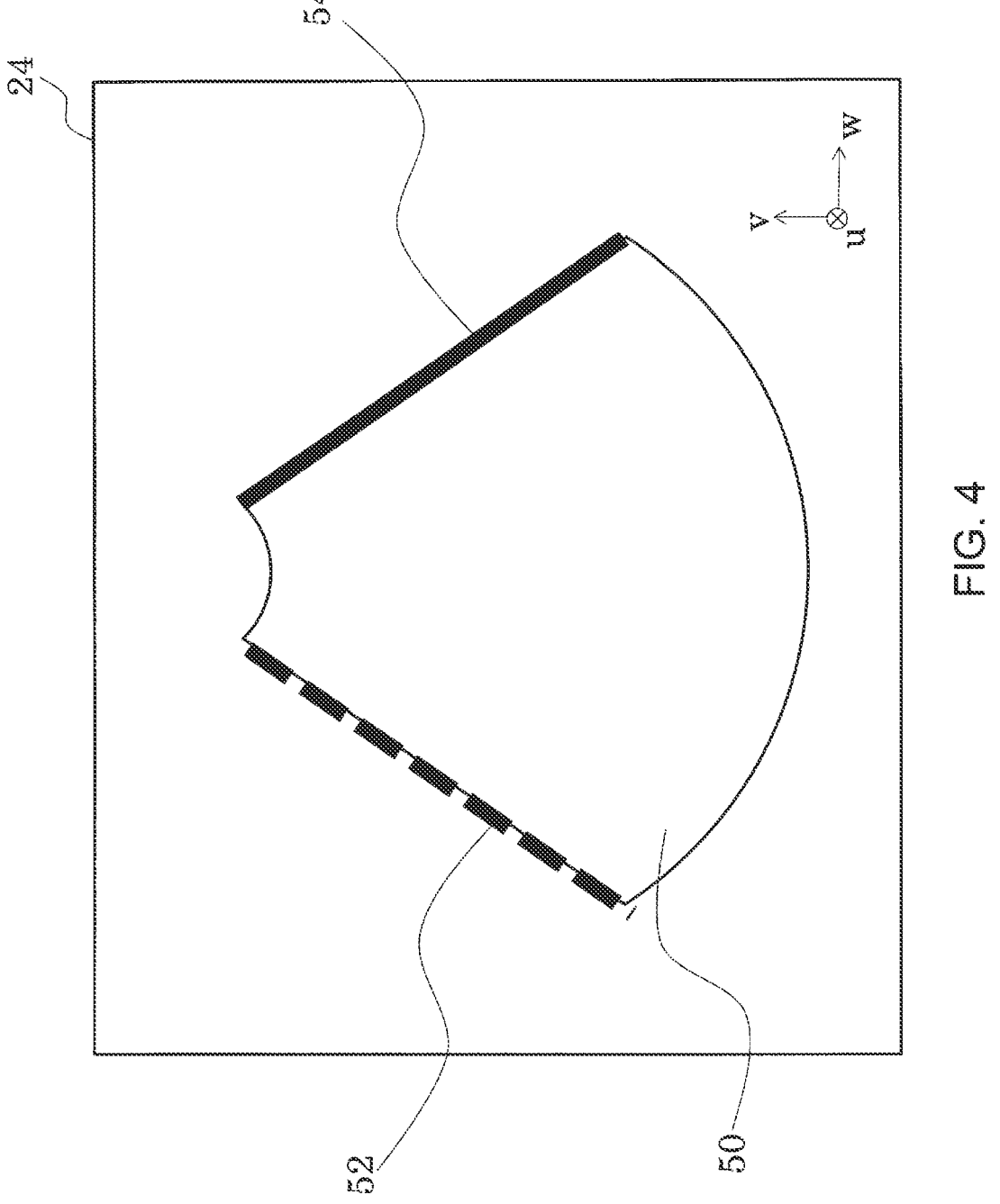
FIG. 4 is a diagram illustrating an example of a B-mode image which is displayed on a display device.

FIG. 4 illustrates an example of a B-mode image 50 which is displayed on the display device 24. The B-mode image 50 has a shape of a substantially circular sector shape and represents an image of a body tissue. In the B-mode image 50 in FIG. 4, a left-side boundary line 52 and a right-side boundary line 54 are indicated. The boundary line 52 and the boundary line 54 may be displayed with different colors or different thicknesses or may be displayed with different kinds (kinds such as a solid line, a broken line, and a one-dot chain line). In the example illustrated in FIG. 4, the boundary line 52 is indicated by a broken line, and the boundary line 54 is indicated by a solid line. Colors of the left-side boundary line 52 and the right-side boundary line 54 may respectively be the same as the colors provided to the left side surface and the right side surface of the probe distal end 32.

Further, in the example illustrated in FIG. 4, together with the B-mode image 50, each axis of a uvz coordinate system is indicated. It is indicated that a direction from the left-side boundary line 52 to the right-side boundary line 54 is the w-axis positive direction; that is, a direction from the left side surface to the right side surface of the ultrasound probe 10.

Such an image display process is performed by combining the B-mode image data with boundary line image data representing a boundary line image such that the boundary line image representing the boundary lines 52 and 54 is superimposed on the B-mode image. That is, the HIFU control unit 26 causes the display device 24 to display an image based on image data in which the B-mode image data and the boundary line image data are combined together.

As described above, the HIFU control unit 26 acts as an image display processing unit and configures, together with the display device 24, an ultrasound image display device. The HIFU control unit 26 generates the B-mode image data based on the ultrasound wave received by the ultrasound probe 10 and causes the display device 24 to display the B-mode image based on the B-mode image data. The HIFU control unit 26 causes the ultrasound image to include the boundary lines 52 and 54 as figures which indicate a correspondence between a direction on the observation surface and a direction on the probe distal end 32.

In such an image display process, a direction in which a front surface of the ultrasound probe 10 is directed is easily perceived by the user by the indicators provided to the probe distal end 32, and a correspondence between the structure of the ultrasound probe 10 and a surface through which the B-mode image is observed is easily perceived by the user.

REFERENCE SIGNS LIST

1 HIFU radiation system
2 ultrasonic transducer
10 ultrasound imaging probe
12 HIFU transducer unit
14 coupling bag
16 transducer housing
18 robot arm
18a arm
18b joint
20 movable body
22 controller
24 display device
26 HIFU control unit
28 robot control unit
30 patient
32 probe distal end
40 support portion
50 B-mode image
52, 54 boundary line

What is claimed is:

1. An ultrasound imaging probe for a HIFU radiation device, comprising:
   a probe distal end to and from which an ultrasound wave is transmitted and received, and
   a coupling bag formed of a light transmitting material and configured to retain a liquid between the probe distal end and a patient, the probe distal end being located inside the coupling bag, wherein
   when a surface where the ultrasound wave is transmitted and received in the probe distal end is defined as a lower surface, a front surface, a rear surface, a left side surface, and a right side surface of the probe distal end are colored with different colors from each other, and
   the ultrasound imaging probe is configured to be transported by a transport mechanism.

2. The ultrasound imaging probe according to claim 1, wherein the probe distal end has the front surface and the rear surface which are colored with complementary colors to each other, or has the left side surface and the right side surface which are colored with complementary colors to each other.

3. An ultrasound image display device for a HIFU radiation device, the ultrasound image display device comprising:
   the ultrasound imaging probe according to claim 1; and
   an image display processing unit which generates image data based on an ultrasound wave received by the ultrasound imaging probe and displays an ultrasound image based on the image data, wherein
   the image display processing unit causes the ultrasound image displayed on the image display processing unit to include figures which indicate a correspondence between a direction on an observation surface through which the ultrasound image is acquired and a direction on the probe distal end.

4. The ultrasound image display device according to claim 3, wherein the figures displayed on the image display processing unit include a left-side boundary line and a right-side boundary line.

5. The ultrasound imaging probe according to claim 1, wherein the color of the front surface or of the rear surface has a relationship of an angle of 90 in a color circle with respect to the color of the left side surface or of the right side surface.

6. An ultrasound imaging probe for a HIFU radiation device, comprising a probe distal end to and from which an ultrasound wave is transmitted and received, wherein in the probe distal end, one of housing surfaces is provided with a color serving as an indicator that indicates an orientation of an observation surface through which an ultrasound image is acquired;

the probe distal end has, in the housing surfaces, a pair of housing surfaces facing opposite directions;

one of the pair of housing surfaces and the other of the pair of housing surfaces are colored with complementary colors to each other, the complementary colors being a combination of two chromatic colors; and the ultrasound imaging probe is configured to be transported by a transport mechanism.

7. The ultrasound imaging probe according to claim 6, comprising a coupling bag which retains a liquid between the probe distal end and a patient, wherein the coupling bag is formed of a light transmitting material.

8. An ultrasound image display device for a HIFU radiation device, the ultrasound image display device comprising:

the ultrasound imaging probe according to claim 6; and an image display processing unit which generates image data based on an ultrasound wave received by the ultrasound imaging probe and displays the ultrasound image based on the image data, wherein the image display processing unit causes the ultrasound image displayed on the image display processing unit to include figures which indicate a correspondence between a direction on the observation surface through which the ultrasound image is acquired and a direction on the probe distal end.

9. An ultrasound image display device for a HIFU radiation device, the ultrasound image display device comprising:

an ultrasound imaging probe including:

a probe distal end to and from which an ultrasound wave is transmitted and received; and a coupling bag formed of a light transmitting material and configured to retain a liquid between the probe distal end and a patient, the probe distal end being located inside the coupling bag, wherein when a surface where the ultrasound wave is transmitted and received in the probe distal end is defined as a lower surface, a front surface, a rear surface, a left side surface, and a right side surface of the probe distal end are colored with different colors from each other, the ultrasound imaging probe being configured to be transported by a transport mechanism, the device further comprising:

an image display processing unit which generates image data based on an ultrasound wave received by the ultrasound imaging probe and displays an ultrasound image based on the image data, wherein the image display processing unit causes the ultrasound image displayed on the image display processing unit to include figures which indicate a correspondence between a direction on an observation surface through which the ultrasound image is acquired and a direction on the probe distal end, and wherein the figures displayed on the image display processing unit include a left-side boundary line and a right-side boundary line, and wherein at least one of the left-side boundary line or the right-side boundary line has a color that is the same as the color of the left side surface or the right side surface, respectively, of the surface.

* * * * *